(12) United States Patent
Scurtescu et al.

(10) Patent No.: US 10,265,547 B2
(45) Date of Patent: Apr. 23, 2019

(54) INTERNAL ULTRASOUND GEL

(71) Applicant: SmileSonica Inc., Edmonton (CA)

(72) Inventors: Cristian Scurtescu, Edmonton (CA);
Vishal Kanda, Edmonton (CA); Pascal Bisson, Edmonton (CA)

(73) Assignee: SMILESONICA INC., Edmonton (CA)

( * ) Notice: Subject to any disclaimer, the term of this patent is extended or adjusted under 35 U.S.C. 154(b) by 0 days.

(21) Appl. No.: 14/653,196

(22) PCT Filed: Dec. 18, 2013

(86) PCT No.: PCT/CA2013/001058
§ 371 (c)(1),
(2) Date: Jun. 17, 2015

(87) PCT Pub. No.: WO2014/094127
PCT Pub. Date: Jun. 26, 2014

(65) Prior Publication Data
US 2015/0335916 A1    Nov. 26, 2015

Related U.S. Application Data

(60) Provisional application No. 61/740,408, filed on Dec. 20, 2012.

(51) Int. Cl.
*A61K 31/047* (2006.01)
*A61N 7/00* (2006.01)
*A61K 49/22* (2006.01)
*A61B 8/12* (2006.01)
*A61B 8/00* (2006.01)

(52) U.S. Cl.
CPC .......... *A61N 7/00* (2013.01); *A61B 8/12* (2013.01); *A61B 8/4281* (2013.01); *A61K 31/047* (2013.01); *A61K 49/226* (2013.01)

(58) Field of Classification Search
None
See application file for complete search history.

(56) References Cited

U.S. PATENT DOCUMENTS

| | | | | |
|---|---|---|---|---|
| 4,002,221 A | * | 1/1977 | Buchalter | A61B 5/04087 181/0.5 |
| 5,482,965 A | * | 1/1996 | Rajadhyaksha | A61K 8/41 514/452 |
| 7,004,933 B2 | | 2/2006 | McDaniel | |
| 7,070,565 B2 | | 7/2006 | Vaezy et al. | |
| 7,078,015 B2 | | 7/2006 | Unger | |
| 7,269,873 B2 | | 9/2007 | Brewer et al. | |
| 7,285,093 B2 | | 10/2007 | Anisimov et al. | |
| 8,273,024 B2 | * | 9/2012 | Chew | A61B 8/4281 600/437 |
| 2001/0052740 A1 | * | 12/2001 | Woo | G11B 17/22 312/9.45 |
| 2005/0171419 A1 | * | 8/2005 | De Ziegler | A61K 49/226 600/407 |
| 2006/0281045 A1 | | 12/2006 | Ariff et al. | |
| 2008/0281197 A1 | * | 11/2008 | Wiley | A61B 8/4281 600/437 |
| 2008/0311545 A1 | | 12/2008 | Ostler et al. | |
| 2009/0099149 A1 | * | 4/2009 | Liu | A61K 9/006 514/182 |
| 2009/0297441 A1 | * | 12/2009 | Canham | A61K 49/0043 424/1.61 |
| 2010/0124732 A1 | | 5/2010 | Ariff et al. | |
| 2012/0040312 A1 | | 2/2012 | Hinders | |
| 2012/0150033 A1 | * | 6/2012 | Rauch | A61B 8/4281 600/437 |

FOREIGN PATENT DOCUMENTS

| | | |
|---|---|---|
| CA | 2312614 A1 | 1/2001 |
| CA | 2484869 | 11/2003 |
| CA | 2770837 A1 | 2/2011 |
| CN | 101716354 | 6/2010 |
| CN | 102107013 | 6/2011 |
| WO | 2003094710 | 11/2003 |
| WO | 2011134071 | 11/2011 |

OTHER PUBLICATIONS

Lubrizol Polmers (https://www.lubrizol.com/en/Life-Sciences/Regulatory/US-FDA-Inactive-Ingredient-Database (downloaded Apr. 24, 2017).*
Parker Laboratories (http://ekkomed.dk/en/index.php?controller=attachment&id_ attachment=100 (2009)).*
Wikipedia_Methylparaben (https://en.wikipedia.org/wiki/Methylparaben (downloaded Jun. 19, 2018)).*
Doyle et al (Sodium Reduction and Its Effect on Food Safety, Food Quality, and Human Health. Comprehensive Reviews in Food Science and Food Safety. vol. 9, Issue1 Jan. 2010. pp. 44-56).*
Makinen, K. K. and Soderling, E. 1981. "Effect of Xylitol on Some Food-Spoilage Microorganisms", Journal of Food Science. 46:950.
Kontiokari, T. et al. 1995. "Effect of Xylitol on Growth of Nasopharyngeal Bacteria In Vitro", Antimicrobial Agents and Chemotherapy. 39:1820.

(Continued)

*Primary Examiner* — Jake M Vu
(74) *Attorney, Agent, or Firm* — Marsh Fischmann & Breyfogle LLP; Jonathon A. Szumny

(57) ABSTRACT

An ultrasound gel is provided for use with internal ultrasound imaging and/or therapy. The gel can have acoustic properties that can closely match a soft tissue to be imaged/treated and can be of a high viscosity that is maintained when heated by the body. In some embodiments, the gel can act as a lubricant and, although water based, can be hydrophobic and not dissolve in bodily fluids. In some embodiments, the gel can be sterile, safe for ingestion, and include a preservative. The gel can be used for oral or non-oral applications and when used orally, can comprise a dental agent for inhibiting growth of dental microorganisms and/or prevent respiratory infections.

11 Claims, 1 Drawing Sheet

(56) References Cited

OTHER PUBLICATIONS

Lubrizol "Ultrasound Gel with Carbopol ® 980 NF Polymer", Lubrizol Advanced Materials Inc. Jun. 1, 2011.
Söderlin "Xylitol, Mutans Streptococci and Dental Plaque", Adv. Dent. Res 2009, 21: 74-78, Aug. 2009.
The Lubrizol Corporation: "Oral Suspensions", Pharmaceutical Bulletin 22, Edition May 23, 2011.
Lubrizol "Ultrasound Gel with Carbopol ® ETD 2020 NF Polymer", Lubrizol Advanced Materials Inc. Jun. 1, 2011.

* cited by examiner

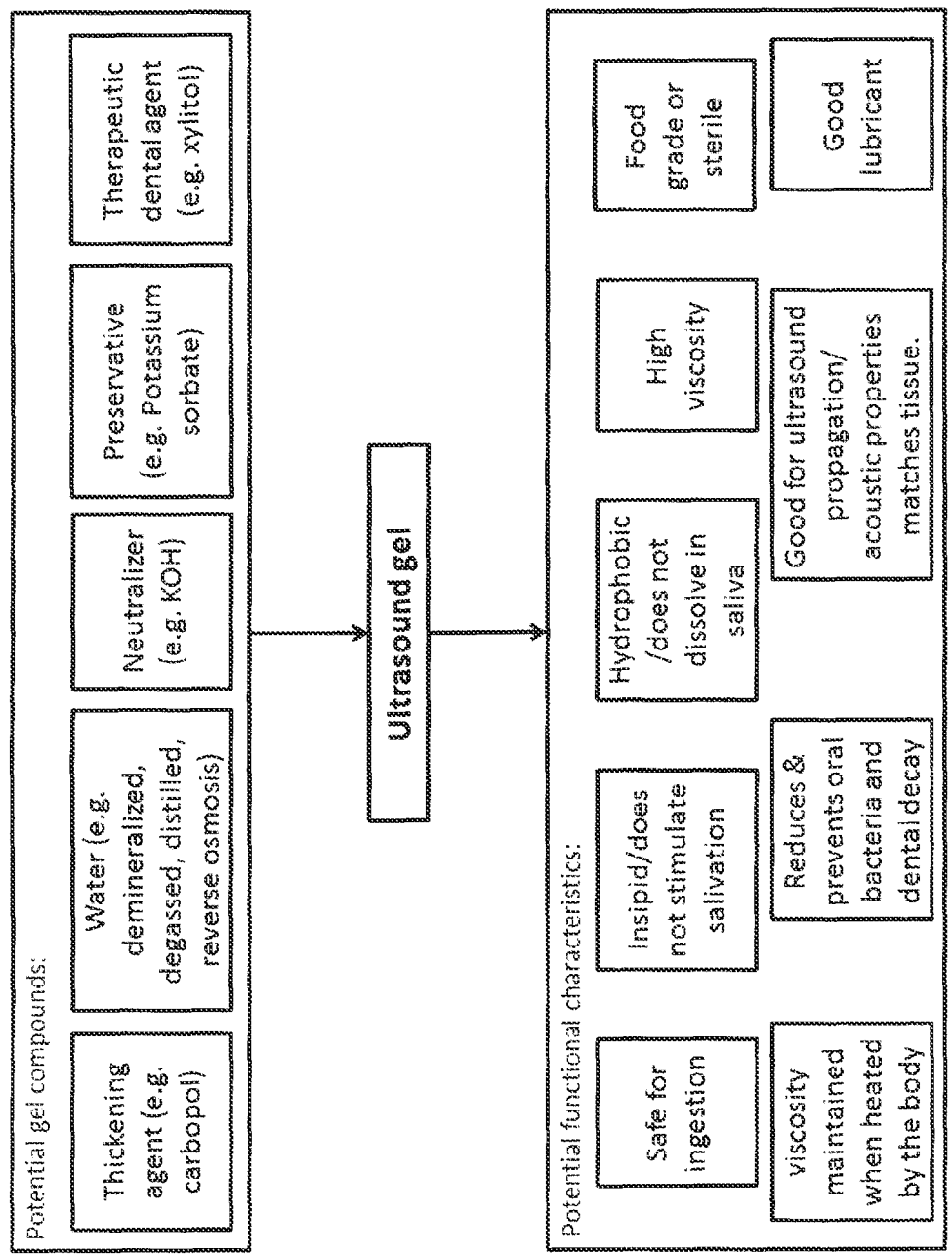

INTERNAL ULTRASOUND GEL

CROSS-REFERENCE TO RELATED APPLICATIONS

This application is a 371 of International App. No. PCT/CA2013/001058, entitled "Internal Ultrasound Gel," and filed on Dec. 18, 2013, which claims priority to U.S. Provisional Application No. 61/740,408, entitled "Internal Ultrasound Gel", and filed on Dec. 20, 2012; the entireties of the aforementioned applications are incorporated herein by reference as if set forth in full.

TECHNICAL FIELD

The present application relates to ultrasound gels, and more particularly, ultrasound gels that can be safely used internally and orally.

BACKGROUND

By way of background, it is standard practice to use aqueous gels as coupling agents for ultrasound producing/sensing devices in ultrasound imaging and therapy. A key element of an ultrasound gel is to have acoustic impedance similar to that of soft tissue.

Some ultrasound therapies and imaging are done intracavitarily or otherwise internally to a patient. For example, ultrasonic dental therapy or imaging devices require the patient to apply the gel intra-orally, however there is presently no ultrasonic gel product specifically approved and labelled for intra-oral applications available on the market. While there are existing non-ultrasonic intra-oral gels, the gels are still labelled as "not to be ingested". The use of a gel with ultrasonic dental therapy or imaging devices requires the patient to apply the gel intra-orally, which can lead to ingestion of small quantities of gel.

There remains a need to provide products and methods, such as internally and orally compatible ultrasound gels, that can overcome the shortcomings of the prior art.

SUMMARY

The present disclosure relates to an ultrasound gel for use with internal and oral ultrasound imaging and/or therapy. The gel can have ultrasound acoustic properties that can closely match a soft tissue to be imaged/treated and can be of a high viscosity that is maintained when heated by the body or exposed to bodily fluids (for instance, saliva). In some embodiments, the gel can act as a lubricant. Although water-based, the gel can be hydrophobic and not dissolve in bodily fluids. In some embodiments, the gel can be sterile, safe for ingestion, and include a preservative. The gel can be used for oral or non-oral applications and when used orally, can comprise a dental agent for inhibiting growth of dental microorganisms.

In some embodiments, the gels can provide an ultrasound couplant and device lubricant suitable for medical use of ultrasound acoustic energy for intra-oral and dental therapy, imaging or other measurements, while contacting the intra-oral, dental tissue or food pipe tissue, fluids and neighbouring/adjacent organs. The gel can have acoustic properties similar to soft tissue or gums, or other internal bio-structures.

Broadly stated, in some embodiments, an internal ultrasound gel is provided, comprising: water; a thickening agent for thickening the water into a gel; a neutralizer for setting the gel viscosity and adjusting the pH and reacting with the thickening agent in order to set the viscosity of the gel; and a preservative for preserving the gel; wherein the gel has an acoustic impedance similar to soft tissue and can be safely used internally or orally.

Broadly stated, in some embodiments, a method of imaging a tissue with ultrasound is provided, the method comprising: providing an ultrasound imaging apparatus, the apparatus comprising a transducer for emitting ultrasound; applying the ultrasound gel, as described herein, between the transducer and the tissue to be imaged; positioning the transducer proximate the tissue to be imaged; and emitting ultrasound through the gel to image the tissue.

Broadly stated, in some embodiments, a method of treating a tissue with ultrasound is provided, the method comprising: providing an ultrasound treatment apparatus, the apparatus comprising a transducer for emitting ultrasound; applying the ultrasound gel, as described herein, between the transducer and the tissue to be treated; positioning the transducer proximate the tissue to be treated; and emitting ultrasound through the gel to treat the tissue.

Broadly stated, in some embodiments, a kit for applying ultrasound to a tissue is provided, the kit comprising, the ultrasound gel, as described herein, and instructions for use of the gel.

BRIEF DESCRIPTION OF THE DRAWINGS

FIG. 1 is a schematic block diagram depicting an embodiment of an ultrasound gel.

DETAILED DESCRIPTION OF EMBODIMENTS

An ultrasound gel is provided for use with internal ultrasound imaging and/or therapy. The gel can have acoustic properties that can closely match a soft tissue to be imaged/treated and can be of a high viscosity that is maintained when heated by the body. In some embodiments, the gel can act as a lubricant. The gel although water based, can be hydrophobic and not dissolve in bodily fluids. In some embodiments, the gel can be safe for ingestion, is sterile, and include a preservative. The gel can be used for oral or non-oral applications and when used orally, can comprise a dental agent for inhibiting growth of dental microorganisms.

Referring now to FIG. 1, a schematic block diagram is shown depicting possible components and potential functional characteristics of an embodiment of an ultrasound gel. In some embodiments, the ultrasound gel can comprise a thickening agent, water, a neutralizer, a preservative, and a dental agent. In some embodiments, the ultrasound gel can be safe for ingestion, insipid, hydrophobic, of high viscosity that can be maintained when heated, food grade and/or sterile, reduce and prevent oral bacteria and dental decay, good for ultrasound propagation/acoustic properties match soft tissue, and also be a good lubricant.

In some embodiments, the gel can be used as a medical ultrasound coupling media and lubricant. The gel can possess certain properties as outlined herein.

In some embodiments, the gel can be biocompatible, orally compatible, and ingestible by humans or animals. The components of the gel can be based on the U.S. Food and Drug Administration (FDA) Generally Recognized as Safe (GRAS) list for acceptable ingredients and food additives. In some specific embodiments, the gel components can be Carbopol™ 974P NF, water, potassium sorbate, potassium hydroxide, xylitol, with an acidity at a non-irritating level (for example, between pH 5.5 and 7.0, and in some embodiments, pH 6.0). As all gel components can be safe for ingestion, if a patient ingests the gel accidentally or intentionally, the gel will be safe. In some embodiments, the gel can be food grade, following good manufacturing practice (GMP) or natural health products (NHP) standards, or sterile. The gel can be sterilized by heat (for example, by autoclaving) or other sterilization methods as known in the art (for example, by e-beam or gamma irradiation). In sterile embodiments, the gel can also be used on open wounds. In some embodiments, the gel can be safe for long term repeated ingestion. For example, users can ingest small quantities (a few mL) daily without adverse effects as per FDA's GRAS database. The gels can be excretable by natural pathways or processes. In some embodiments, the gels also do not adversely affect tooth health, gum tissue, or corrode teeth.

In some embodiments, the gel formulation may require additional compounds in order to maintain its integrity through sterilization, for example gamma radiation sterilization. These stability compounds can be those as known in the art, for example glycerine (glycerol) or propylene glycol. Glycerol has very low toxicity when ingested and it is used widely in foods, beverages and personal care preparations. The oral toxicity of propylene glycol is also very low, and it does not cause sensitization. Glycerol and propylene glycol can also be compatible (and not damage) ultrasound transducer encapsulation such as commonly used silicone.

In some embodiments, a small amount of glycerol (from a few percent to a few tens of percent) can be used to enhance gel resistance to breaking down under larger doses of gamma radiation. For oral use of a gel, a low glycerol concentration (for example, 5%-10%) can be used without significantly sweetening the gel, while allowing the gel to withstand larger dose of gamma radiation (for example 40 kGy) and maintaining the high viscosity of the gel.

A low glycerol concentration (5%-10%) can also cause a negligible increase in the acoustic impedance of the gel therefore maintaining an acoustic impedance closely similar to that of soft tissue (approximately 1.5 MRayl), which can be important for ultrasound wave propagation to minimize transducer-gel-tissue interface ultrasound reflections.

In addition, some embodiments of the gels can also be safe for use with ultrasound transducer equipment, such as ultrasound transducers and transducer heads known to those skilled in the art (including materials such as silicone elastomers, epoxy, or plastic, for instance). Accordingly, the gels can be used with ultrasound equipment without causing damage to the equipment. In some embodiments, the gel can be complementary to, and easily incorporated within, intra-oral ultrasonic devices and emerging ultrasonic dental imaging systems.

In some embodiments, the gels can have antimicrobial properties. For example, the gels can resist microbial growth after the gel package/bottle is opened, and after possible contamination by the environment or end user. In some embodiments, a preservative can be used to inhibit molds, yeasts and bacteria in the gel. In some embodiments, the gels can have a long shelf life at room temperature. When under proper conditions, some embodiments of the gel can be shelf-stable and will not physically degrade/decompose at room temperature for a period of approximately at least two years and can also be resistant to microbial spoilage for approximately at least two years.

In some embodiments, the gel can both comprise a preservative and also be sterilized as discussed herein. In these embodiments, the combination of preservative and sterilization can provide for additional safety for usage in internal or oral applications.

In some embodiments, the gels can have a high viscosity as would be understood by one skilled in the art. Viscosity can be difficult to quantify and measure and the measurement can be dependent on the measuring apparatus used and the conditions under what the viscosity is measured. Having said that, one skilled in the art would have a working knowledge of the relative viscosity of a gel with high viscosity. The viscosity and pH can be of an appropriate level to be comfortable and non-irritating to a user. In addition, in some embodiments, the viscosity of the gel is not significantly affected/reduced when the gel heats up in contact with tissue/gums/saliva. The gel can also be able to withstand environments it is exposed to during ultrasound imaging/treatment without a change in viscosity characteristics. Gel viscosity and acoustic impedance can continue to be within acceptable imaging/treatment ranges even after use as intended.

The gel can act as an ultrasound couplant and the high viscosity can provide good acoustic coupling to tissues such as gums and allow for the gel to stay in place when positioned. As such, the gel can enhance the desired acoustic properties of the applied ultrasound devices and/or treatments. The ultrasound gel can have similar acoustic properties to the tissue it couples to, as ultrasound (sounds of a frequency higher than 20 kHz) propagates poorly through air.

In some embodiments, the gels can be tasteless (insipid) and do not stimulate salivary glands. The absence of taste in the mouth can reduce salivation which assists in reducing the amount of gel being washed by saliva and potentially ingested. Slight fragrance or flavors in the mouth can provide an increase in salivation which can be undesirable. In addition, the absence of taste can allow users to tolerate the gel in their mouths. In some embodiments, the gel can be mildly unpleasant in the mouth. As such, patients/users would be less likely to intentionally consume the gel.

In some embodiments, the gel manufacturing process can be done under vacuum to reduce/eliminate air trapped in the gel. The gel can be produced free of, or with a reduced amount of, air bubbles. In some embodiments, this characteristic can be achieved by vacuum mixing and manipulation during manufacturing.

Undissolved polymer or other insoluble particulate material can be avoided by thorough mixing, general adherence to GMP practices, and by using high grade compounds such as use of National Formulary (NF) standard compounds.

To achieve some or all of these properties, in some embodiments, the gel can comprise water, a neutralizer, a gelling/thickening agent, a preservative, a dental agent, and/or a colourant. In some embodiments, the colorant can be, for example, FD&C (Food, Drug, and Cosmetic) Green 3 colour powder, although any other safe coulorant known in the art could be used.

In some embodiments, the gel can be water-based, but not water soluble (hydrophobic) and therefore not dissolved by saliva. In addition, some embodiments of the gel do not dry out easily. In some embodiments, the water used in the gel can be demineralized, degassed, distilled and/or reverse osmosis. In addition, the water can be free of salts or alkali, as the presence of electrolyte can significantly reduce the viscosity of the gel. The water used in the gel can have low or acceptable levels of minerals, bacteria, etc. as would be known in the art.

In some embodiments, a neutralizer can be used to neutralize the pH of the gel to a biologically acceptable level. In some embodiments, a base can be used as a neutralizer, for instance potassium hydroxide (KOH), sodium hydroxide (NaOH), or triethanolamine. An appropriate amount of base can be used to obtain a final gel pH similar to saliva, in the range of 6+/−1, or in the range of 6+/−0.5. In some embodiments, KOH can be used (instead of NaOH) in order to minimize the viscosity loss/reduction due to the neutralizer, thereby maintaining high viscosity of the gel.

In some embodiments, the gel formulation can contain a gelling/thickening agent to increase the viscosity of the gel. In some embodiments, the gelling/thickening agent can be a carbomer. In some cases, the carbomer can be a Carbopol™. As known in the art, there are a variety of Carbopol polymer grades which differ in the performance characteristics (U.S. Pat. No. 4,002,221 by Buchalter, incorporated by reference herein in its entirety). In some cases, the Carbopol™ can be a highly cross-linked polymer such as a Carbopol™ 974P NF. Carbopol™ 974P NF can provide low irritancy and non-sensitizing properties. In addition, Carbopol™ 974P NF is generally not bio-absorbed or metabolized in the body due to the high molecular weight and can be cross-linked exhibiting high viscosities. Carbopol 974P NF concentrations of 0.1% to 5% by weight in the gel can be used in some embodiments to provide suitable viscosity for oral use. As known in the art, these percentages can be measured as being relative to the weight of the water. That is, adding 1 gram of polymer to 100 grams of water would likely be known to those versed in the art as "1%". It can also be possible however, that one could have an alternate opinion, that a 1% solution is 1 gram dissolved in 99 grams of water, as this would have a total mass of 100 grams, giving what may be interpreted as a 1% solution. In this case, either interpretation can be allowed. In some embodiments, the Carbopol 974P NF™ concentration can be 1.3% by weight in the gel.

In some embodiments, a preservative can also be added to the gel to preserve the gel and increase its safety for internal ultrasound applications. In some embodiments, the preservative can be a food grade preservative, for example, potassium sorbate, parabens, or monolaurin. Potassium sorbate can be used in the range of 0.01% to 1% of the gel to provide suitable preservation against common pathogens for a pH in the range of 3 to 6.5, or in the range of 6+/−0.5, which is also a common acidity range for saliva. In addition, other preservatives such as parabens can be used if a higher pH range is desired (for example, from pH 3 to 9). In some embodiments, the potassium sorbate concentration can be 0.1%. An acceptable daily ingestion intake of potassium sorbate can be 875 mg daily for an average adult of 70 kg. For some oral applications, only few grams of the gel can be used per day (for example, an estimated 3-5 grams per day). Assuming full ingestion and a potassium sorbate concentration of 0.1% of the gel, the daily dose would be on the order of few milligrams, which is well below the acceptable daily ingestion of 875 mg.

In some embodiments, a dental agent can be used in the gel to provide added dental benefits to a user/patient when the gel is used orally. In some embodiments, the dental agent can be a sugar alcohol. In some embodiments, the sugar alcohol can be xylitol. The dental agent can provide an additional treatment/therapeutic effect to a user/patient by preventing/reducing dental/oral bacteria and/or respiratory infections. For preventing dental decay, sugar alcohol, for instance xylitol in the range of 0.1% to 5% has been shown to reduce oral bacterial flora (for example *Streptococcus mutans*) and can lead to reduced risk of dental cavities and improved oral and dental health. A preferred concentration to reduce and prevent dental decay is 0.5% (this concentration was used in Kontiokari, T. et al. 1995. "Effect of Xylitol on Growth of Nasopharyngeal Bacteria In Vitro", Antimicrobial Agents and Chemotherapy. 39:1820, incorporated by reference herein in its entirety). Xylitol was also shown (same reference) to reduce bacteria in nasopharyngeal flora and reducing respiratory infections (for example inhibiting the growth of *Streptococcus pneumonia*). In addition, xylitol is known to also have food preservation properties inhibiting the growth of microorganisms such as clostridium butyricum, lactobacillus bulgaricus, saccharomyces cerevisiae, *Escherichia coli*, salmonella typhi (Makinen, K. K. and Soderling, E. 1981. "Effect of Xylitol on Some Food-Spoilage Microorganisms", Journal of Food Science. 46:950, incorporated by reference herein in its entirety).

In some embodiments, a colorant (food, drug and/or cosmetic grade) could also be added to the gel if a colored gel is desired.

Other concentrations of the gel components can also be used to obtain similar desired properties and results.

With regard to packaging and uses, the gels can be packed in sachet bags (for single or multiple uses), tubes (for single or multiple uses), or in bottles (squeeze bottles or bottle with pump), although any other appropriate packaging and/or dispensing means, as apparent to one skilled in the art, could be used. Prior art gels for internal use are generally available in small, sterile, pouches for single use. These prior art gel formulations risk spoilage and/or contamination with undesired microbes when the package is opened and exposed to air. As such, these prior art gel formulations are limited to single-use packaging. By contrast, some embodiments of the present gels do not have the same risk of spoilage, degradation, or contamination and can be packaged for multiple uses, adding increased convenience for the manufacturer and the user.

In some embodiments, the gel can be used with ultrasound devices for ultrasound imaging and/or ultrasound treatment (therapy). Some examples of uses include methods of intraoral and dental ultrasound treatment (therapy in the oral cavity or the teeth/dental), methods of ultrasound imaging in the oral cavity (tongue, cheek, etc.) or dental ultrasound imaging, methods of internal imaging such as endorectal (transrectal) ultrasonography, transvaginal ultrasonography, or trans-esophageal echocardiography (ultrasound imaging of the heart through the food pipe). In addition, the gels can be used in general (non-ultrasound) dental applications, such as gels to improve denture comfort and as a vehicle for chemical/pharmaceutical agents aimed at improving tooth and gum sensitivity or help the treatment of oral organs or food pipe organs where a gel is required. In some embodiments, imaging/therapy can be performed from outside of a mouth, where the imager/therapist adds gel (an external ultrasound gel as known in the art, or a gel as disclosed herein) in between the transducer and the cheek, and also an oral compatible gel (as disclosed herein) between the cheek and the dental organ for ultrasound coupling for imaging or therapy.

The specific properties of the gels provided herein can provide benefits in these types of applications. For example, the high viscosity of the gel permits the gel to stay on an ultrasound transducer head and reach the target site, whereas prior art gels are washed away or eroded by the body cavity prior to reaching the target site. The gels can be biocompatible with oral, food pipe, vaginal and rectal tissue and fluids.

While the gels and uses thereof described herein are generally applicable to human imaging and therapy, the gels and uses thereof can also be applicable to veterinary ultrasound applications.

Without any limitation to the foregoing, the present method is further described by way of the following examples.

Example 1

Materials

Materials: Purified Water 1100 g, Carbopol 974P NF 13 g, Potassium Hydroxide 18 g, Club House™ green food colour 1 mL, Xylitol 5 g, Potassium sorbate 1 g.

Equipment: Clock/Timer—calibrated, Vacuum pump, 5/16" ID vacuum tubing, Vacuum chamber, Top-loading balance (0.1 g precision), Time-of-flight acoustic measurement system, pH meter+electrode, Brookfield™ viscometer.

General Supplies: Calculator, Spatula, Scoopula, Mixing vessel (eg. large jar or vat), Weighing paper, 50 mL plastic syringe—Luer-lock, Dropper bottle with dropper, KimWipes™, Paper towels, Label sheets, Pen, Felt marker, Anti-static brush, 50 mL beaker, Broad spatula.

Example 2

Production

Note that in some embodiments, mixing steps can be performed under vacuum so as to minimize gas/bubbles in the gel. If water or solutions are not previously degassed, the water or solution can be degassed prior to use so as to minimize gas/bubbles in the gel.

Prepare 18% KOH(aq) neutralizer: Weigh out 100 grams pure water into a small beaker. Weigh out 18 grams solid KOH into a beaker or onto a weighing paper. Slowly add solid KOH to water, allow to dissolve with occasional stirring (glass rod or plastic spatula). When fully dissolved, pour mixture into dropper bottle labelled as "18% KOH(aq)".

Prepare gel dispersion: Weigh out 900 grams water into mixing vessel (eg. 1000 mL beaker). Weigh out 5 grams xylitol. Dissolve xylitol in water with stirring. Weigh out 1 gram potassium sorbate. Dissolve potassium sorbate in xylitol solution above. Weigh out 13 grams Carbopol™ 974P NF. CAUTION: This material is a fluffy, lightweight powder. Ensure that any air currents are minimized and that all weighing surfaces are static free. Static can be minimized by light brushing of contacting surfaces with anti-static brush. Add Carbopol™ powder to potassium sorbate/xylitol solution above, with gentle manual mixing using a spatula. Allow the gel to hydrate, for example by allowing it to sit covered overnight in order to hydrate. *NOTE: the gel hydration can also be sped up by adding the Carbopol™ powder to a spinning volume of water, as with a magnetic stirrer.

Prepare gel: Add 42.9 grams of KOH solution above to a small beaker or other transfer vessel. The neutralizer solution should be added in a weight ratio of 3.3 grams neutralizer per gram of Carbopol™ powder. Add 42.9 grams KOH neutralizer solution to gel dispersion with manual stirring using broad spatula. Mix until homogeneous gel is achieved. *NOTE: the gel will be highly viscous, making convection very difficult. Because of this, the mixing requires a lot of physical mixing. Unless the entire volume of the gel is thoroughly mixed, there will be regions of differing pH. Confirm pH is approximately 6.0 using a standard pH meter. With a pH meter, after calibrating the meter, dip the electrode into the gel and stir it around briefly to coat the electrode in gel, then take a reading. Take a few readings, mixing in between. If the readings are inconsistent, mix the gel thoroughly and check again. If the readings were inconsistent on a sample volume, then it is likely that the entire batch is not properly mixed. Target pH=6.0±0.2. If the pH is low, add neutralizer in appropriate increments until pH is in correct range. Note that the readings will not be consistent without extremely thorough mixing. Add an acceptable colourant to the gel, for example add FD&C (Food, Drug, and Cosmetic) Green 3 colour powder to gel. Mix until colour is evenly dispersed. This will take thorough mixing with a broad spatula, or mixing by pallets in an industrial mixing chamber, under a vacuum.

Degas gel: The degassing step is intended to remove bubbles introduced in the formulation process. Place the gel in an open container. Place this container into the vacuum chamber, seal the chamber, and pump down to 600 mm Hg for 10 minutes (stopwatch). Allow the gel to warm up to room temperature before making any further measurements.

Characterize gel density: Multiple methods to characterize gel density are known in the art and can be used. In one example, draw some degassed gel into a 50 mL syringe, avoiding drawing in air bubbles as much as possible. Use some easily readable part of the piston to make an initial reading of volume. *Note that the total volume is not important, only the difference between the initial and final volume readings. Wipe all excess gel from the outside of the syringe using a paper towel or KimWipe™, then weigh the syringe. Draw some more degassed gel into the syringe, studiously avoiding drawing in air bubbles. The more gel used here, the lower the relative error, so get at least 10 mL of gel on top of the initial amount. Record the final volume measurement using the same part of the piston as was used for the initial measurement. Wipe all excess gel from the outside of the syringe using a paper towel or KimWipe, then weigh the syringe. Typical values are in the range 1.004-1.021 g/mL.

Characterize gel acoustic velocity: Multiple methods to characterize gel acoustic velocity are known in the art and can be used. In one example, using a spatula or something similar, fill the time-of-flight device with gel. One example of an in-house time-of-flight device can be a plastic cylinder with a length of approximately 100 mm, with an ultrasound transducer attached to one end, and a thin sheet of metal attached at the other end. The tube can be filled with gel, the transducer can generate short ultrasound pulses when driven by a function generator, the transducer can sense a returning ultrasound pulse when connected to an oscilloscope, and the thin metal sheet can work as an ultrasound reflector. Place the device in the vacuum chamber and degas as before. There should be no bubbles or air gaps in the gel during the measurement. Using the function generator and digital oscilloscope, record the time of flight. Using the in-house apparatus, typical values for the acoustic velocity can be in the range of 1450-1490 m/s.

Calculate acoustic impedance: Calculations were done based on in-house device although multiple methods to calculate acoustic impedance are known in the art and can be used. In one example, Impedance=(density)(acoustic velocity). Typical values calculated in-house have ranged from 1.45-1.52 MRayls, although other values are possible.

Packaging and Quality Control: Dispense gel into final packaging.

Viscosity testing: The viscosity determined for the gel at pH 6 was 45,000 to 100,000+ mPa·s (or cP), and 60,000 mPa·s (or cP) in one sample [at 25° C. using Brookfield™ LVF, spindle #4, 30 rpm]. This can be a target spec, although deviations may occur in different circumstances and when scaling up production. Viscosity can be difficult to quantify and measure and the measurement can be dependent on the measuring apparatus used and the conditions under what the viscosity is measured. Having said that, one skilled in the art would have a working knowledge of the relative viscosity of a gel with high viscosity.

The scope of the claims should not be limited by the embodiments as set forth in the examples herein, but should be given the broadest interpretation consistent with the description as a whole.

Although a few embodiments have been shown and described, it will be appreciated by those skilled in the art that various changes and modifications can be made to the embodiments described herein. The terms and expressions used in the above description have been used herein as terms of description and not of limitation, and there is no intention in the use of such terms and expressions of excluding equivalents of the features shown and described or portions thereof, it being recognized that the invention is defined and limited only by the claims that follow.

The teachings provided herein can be applied to other methods, not necessarily the method described herein. The elements and acts of the various embodiments described above can be combined to provide further embodiments.

These and other changes can be made to the invention in light of the above description. While the above description details certain embodiments of the invention and describes certain embodiments, no matter how detailed the above appears in text, the invention can be practiced in many ways. Details of the method may vary considerably in their implementation details, while still being encompassed by the invention disclosed herein.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification. Accordingly, the actual scope of the invention encompasses not only the disclosed embodiments, but also all equivalent ways of practicing or implementing the invention.

The above description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. The elements and acts of the various embodiments described above can be combined to provide further embodiments.

While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

REFERENCES

The following references are hereby incorporated by reference into this application in their entirety.
1. Canadian Patent Application Number 2,770,837
2. Canadian Patent Number 2,312,614
3. US Patent Application Number 2006/0281045
4. US Patent Application Number 2008/0311545
5. US Patent Application Number 2010/0124732
6. US Patent Application Number 2012/0040312
7. U.S. Pat. No. 4,002,221
8. U.S. Pat. No. 7,004,933
9. U.S. Pat. No. 7,070,565
10. U.S. Pat. No. 7,078,015
11. U.S. Pat. No. 7,269,873
12. U.S. Pat. No. 7,285,093
13. U.S. Pat. No. 8,273,024
14. Makinen, K. K. and Soderling, E. 1981. "Effect of Xylitol on Some Food-Spoilage Microorganisms", Journal of Food Science. 46:950.
15. Kontiokari, T. et al. 1995. "Effect of Xylitol on Growth of Nasopharyngeal Bacteria In Vitro", Antimicrobial Agents and Chemotherapy. 39:1820.

We claim:

1. A food grade intra-oral ultrasound gel comprising:
water;
a thickening agent for thickening the water into a gel, the thickening agent comprising carbomer 974;
a neutralizer for setting the gel viscosity and adjusting the pH of the gel;
a dental agent for inhibiting growth of dental microorganisms, the dental agent comprising xylitol;
a food grade preservative for preserving the gel, the food grade preservative comprising potassium sorbate; and
an ingestible stability compound for maintaining gel integrity through sterilization;
wherein the gel has an acoustic impedance of soft tissue and is safe for ingestion.

2. The ultrasound gel of claim 1 wherein the neutralizer comprises a base selected from the group consisting of potassium hydroxide, sodium hydroxide, and triethanolamine.

3. The ultrasound gel of claim 1 wherein the pH of the gel is between 5.8 and 6.2.

4. The ultrasound gel of claim 1 further comprising a colourant for colouring the gel.

5. A method of imaging a tissue with ultrasound, the method comprising:
providing an ultrasound imaging apparatus, the apparatus comprising a transducer for emitting ultrasound;
applying the ultrasound gel of claim 1 between the transducer and the tissue to be imaged;
positioning the transducer proximate the tissue to be imaged; and
emitting ultrasound through the gel to image the tissue.

6. A method of treating a tissue with ultrasound, the method comprising:
providing an ultrasound treatment apparatus, the apparatus comprising a transducer for emitting ultrasound;
applying the ultrasound gel of claim 1 between the transducer and the tissue to be treated;
positioning the transducer proximate the tissue to be treated; and
emitting ultrasound through the gel to treat the tissue.

7. A kit for applying ultrasound to a tissue, the kit comprising, the ultrasound gel of claim 1, and instructions for use of the gel.

8. The ultrasound gel of claim 1 wherein the stability compound comprises glycerine.

9. The ultrasound gel of claim 1 wherein the stability compound comprises propylene glycol.

10. The ultrasound gel of claim 1 wherein the sterilization is gamma radiation sterilization.

11. The ultrasound gel of claim 10 wherein the gamma radiation sterilization comprises up to a dosage of 40 KGy.

\* \* \* \* \*